United States Patent
Sorensen et al.

[11] Patent Number: 6,117,149
[45] Date of Patent: Sep. 12, 2000

[54] ROTARY DEVICE AND METHOD FOR REMOVING OPHTHALMIC LENS

[75] Inventors: John T. Sorensen, Costa Mesa; Michael Mittelstein; Soheila Mirhashemi, both of Laguna Niguel, all of Calif.

[73] Assignee: Optex Ophthalmologics, Inc., San Juan Capistrano, Calif.

[21] Appl. No.: 09/248,421

[22] Filed: Feb. 11, 1999

Related U.S. Application Data

[62] Division of application No. 08/658,846, May 31, 1996, Pat. No. 5,871,492, which is a division of application No. 08/421,421, Apr. 11, 1995, Pat. No. 5,690,641, which is a continuation-in-part of application No. 07/984,229, Nov. 30, 1992, Pat. No. 5,437,678.

[51] Int. Cl.[7] ........................................ A61F 9/00
[52] U.S. Cl. ......................... 606/166; 606/107; 606/170
[58] Field of Search ................................. 606/107, 166, 606/170; 128/898

[56] References Cited

U.S. PATENT DOCUMENTS 4,061,146 12/1977 Baehr et al. ........................... 606/107
4,167,944 9/1979 Banko ................................... 606/107

*Primary Examiner*—Michael Buiz
*Assistant Examiner*—Daphna Shai
*Attorney, Agent, or Firm*—Robert D. Buyan; Stout, Uxa, Buyan & Mullins, LLP

[57] ABSTRACT

A system and method for reducing and removing and ophthalmic lens of a mammalian eye. The system includes a rotary lens-reducing probe device of either straight or curved configuration, the probe device comprising a tubular outer sheath through which a rotatable drive shaft extends. A rotating lens-reducing head member is positioned on the distal end of the drive shaft. The head member is configured and constructed to draw a flow of fluid and lens matter into contact therewith, thereby facilitating complete reduction of the entire lens without requiring significant axial (i.e., longitudinal) movement of the probe within the lens capsule. The distal portion of the tubular sheath is preferably configured to shield a portion of the lens-reducing head, during operation, to avoid inadvertent damage to lens capsule. Also, the distal portion of the sheath may be aimed or positioned to direct the flow of fluid and lens matter created by the rotating head in a preferred flow path within the lens capsule. The device may incorporate infusion and/or aspiration for infusing and/or withdrawing fluid and/or debris into/from the eye.

66 Claims, 7 Drawing Sheets

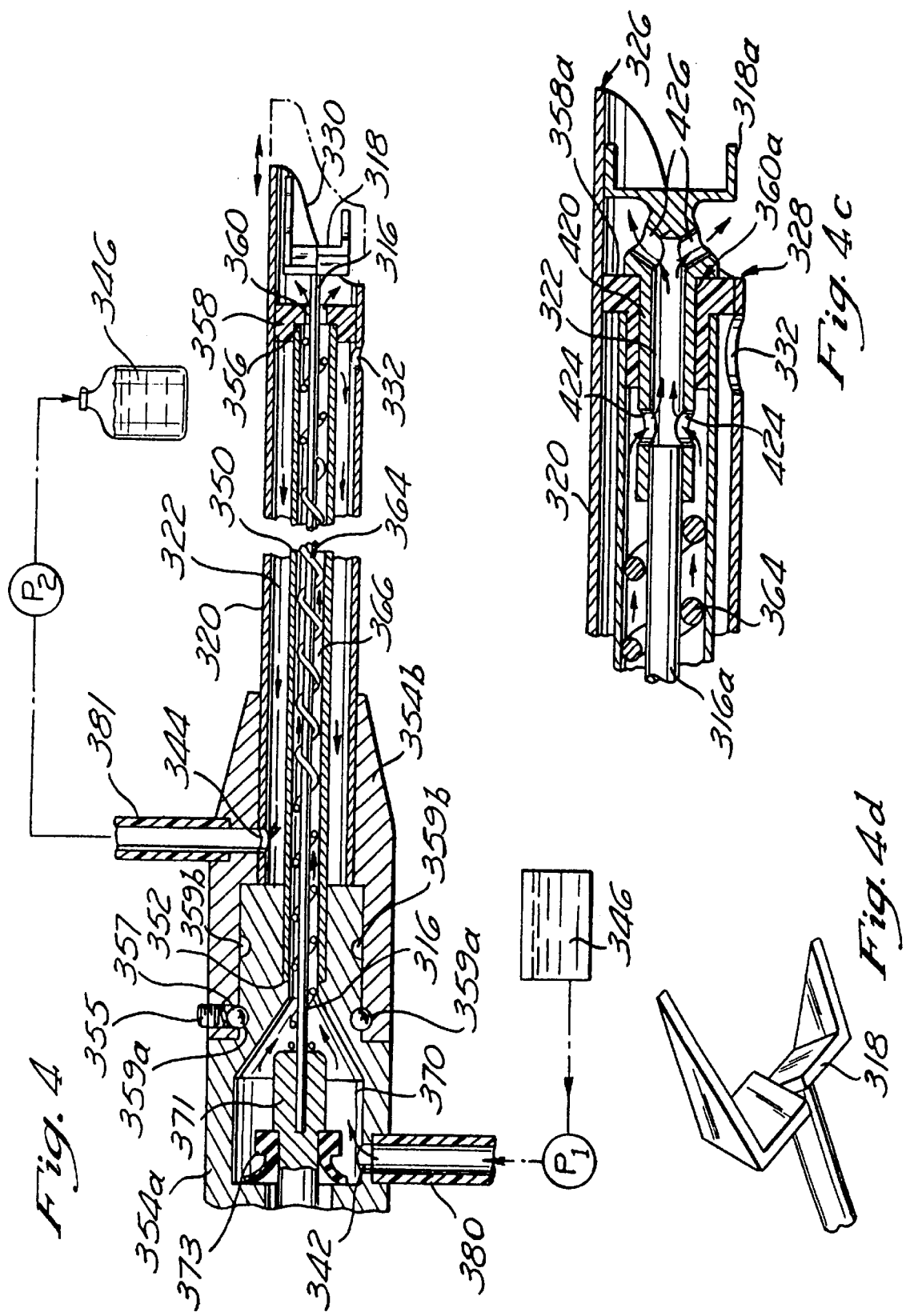

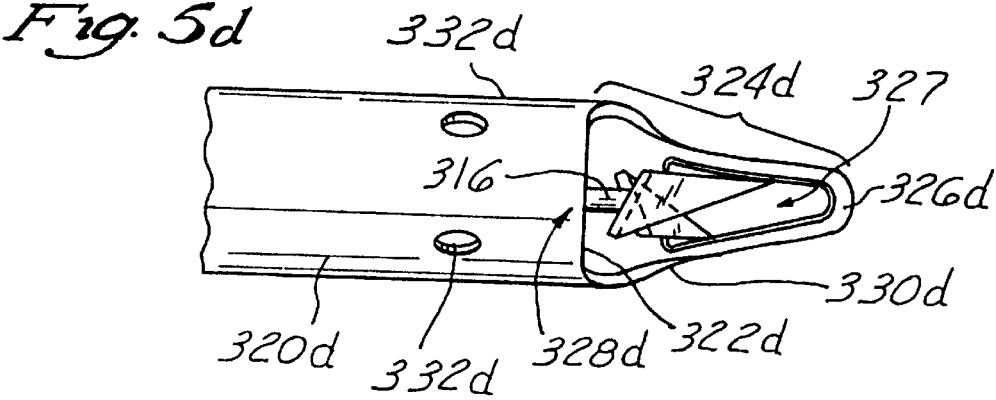
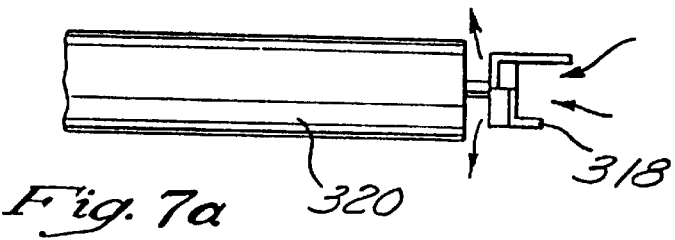
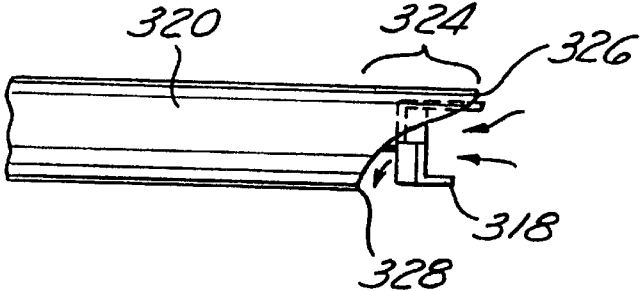
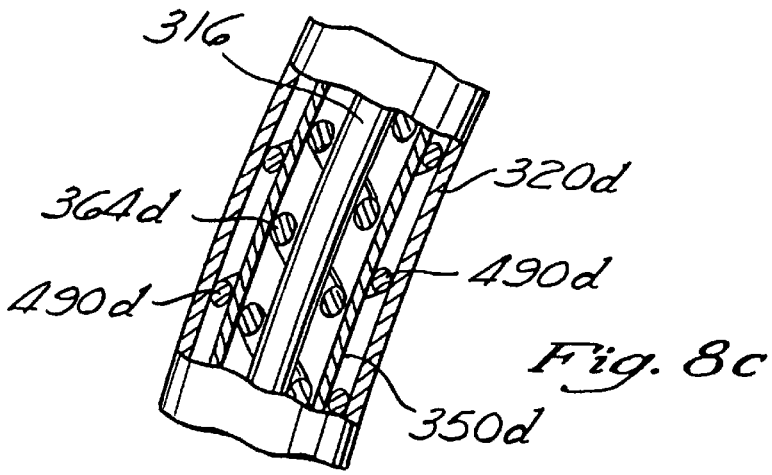

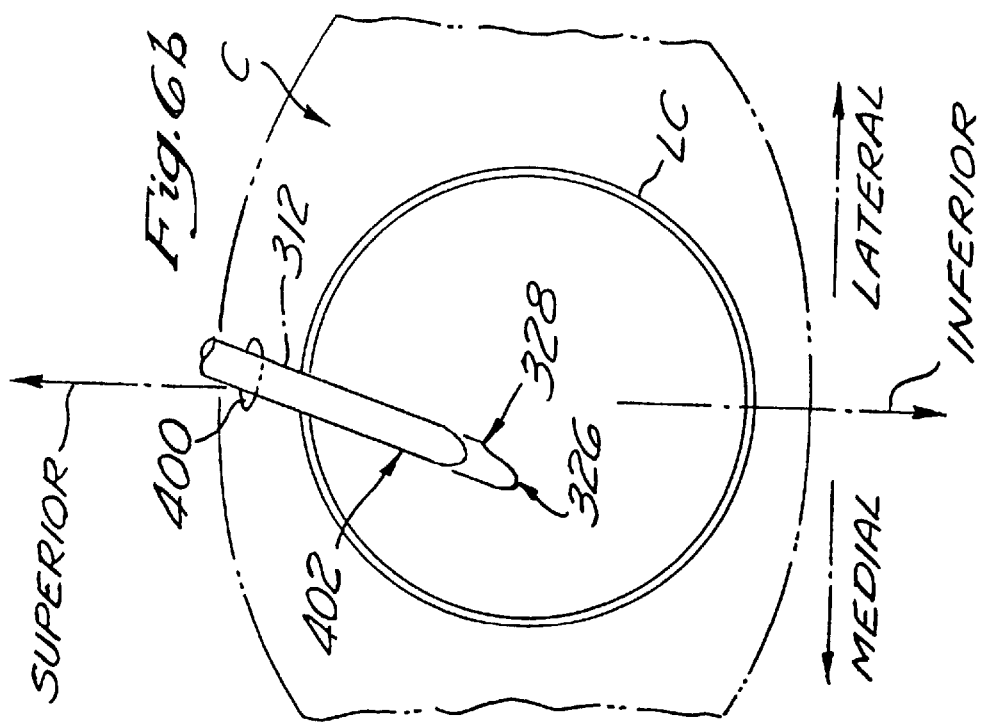
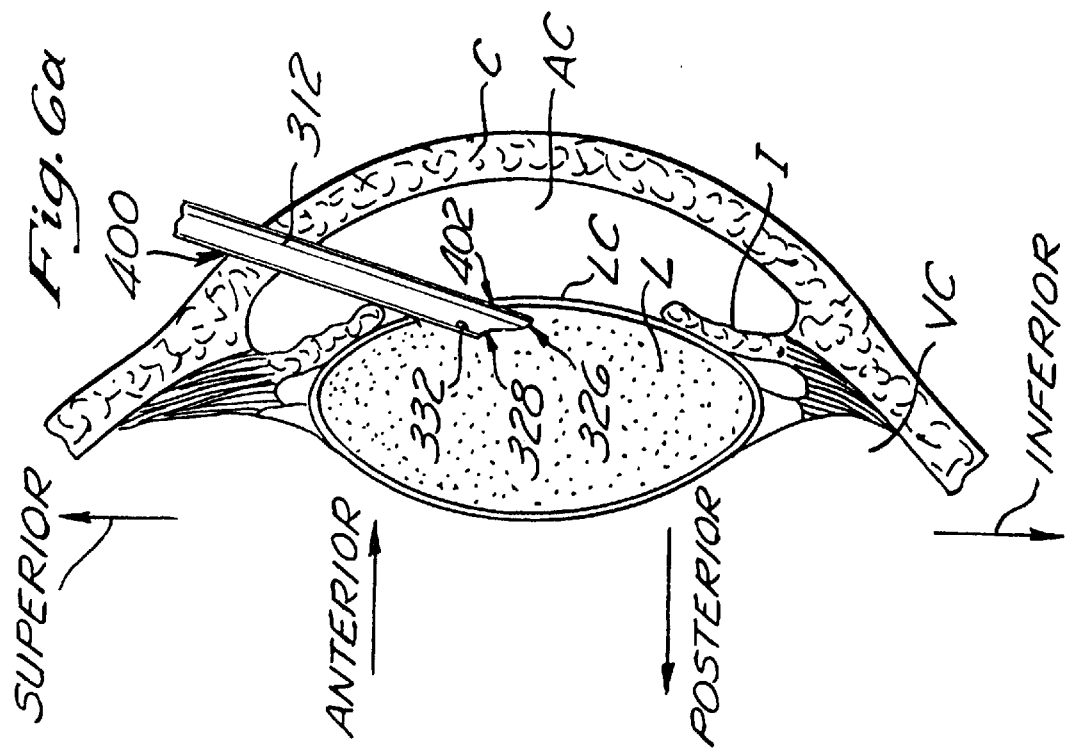

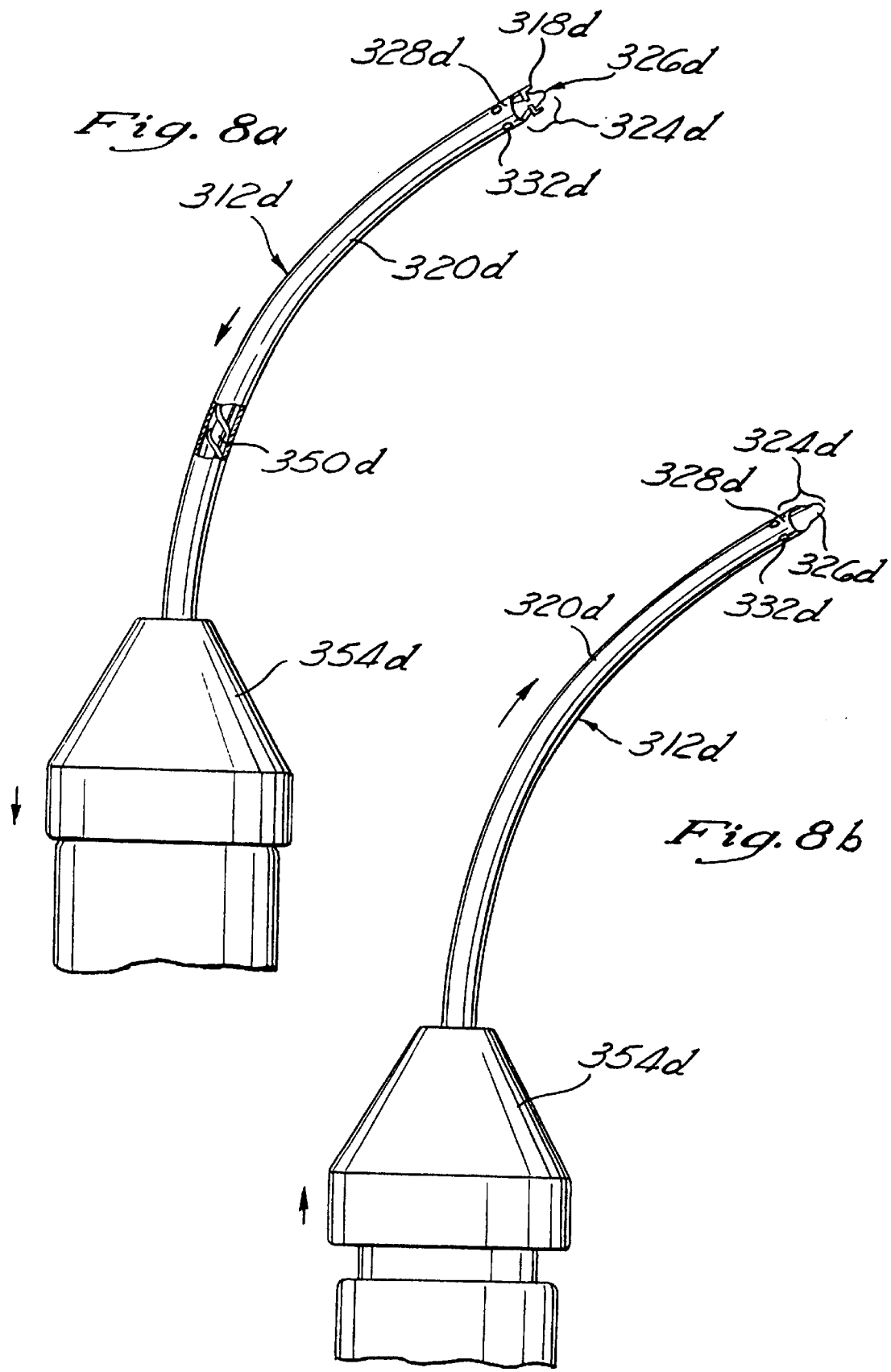

ROTARY DEVICE AND METHOD FOR REMOVING OPHTHALMIC LENS

RELATED APPLICATIONS

This is a division of application Ser. No. 08/658,846 filed on May 31, 1996, now U.S. Pat. No. 5,871,492 which was a division of application Ser. No. 08/421,421 filed on Apr. 11, 1995, now U.S. Pat. No. 5,690,641 which was a continuation-in-part of application Ser. No. 07/984,229 filed on Nov. 30, 1992 now U.S. Pat. No. 5,437,678.

FIELD OF THE INVENTION

This invention relates generally to apparatus and methods for removing ophthalmic lenses and more specifically for removing a cataractous ophthalmic lens for vision restoration.

DISCUSSION OF THE PRIOR ART

The lens of a human eye is a crystalline, transparent biconvex intraocular tissue that helps bring rays of light to focus on the retina. The lens is enclosed in a lens capsule and consists of lens cortex, and lens nucleus. The lens capsule is an elastic bag enveloping the lens and is suspended by fine ligaments (zonule) attached to the ciliary muscles. These muscles radially stretch and relax the capsule thereby varying the optical characteristics of the enclosed lens to provide the desired focus for an image. This is commonly referred to as accommodation.

The lens cortex is a jelly-like portion of the lens and is located between the denser inner nucleus and the elastic outer capsule. The lens nucleus is an optically defined-zone which is denser in the central position of the lens. This nucleus becomes even denser with age, and can eventually harden and fill increasing portions of the total lens space. Additionally the lens may become opacified.

This opacity and cloudiness of the lens commonly referred to as a cataract, may be congenital or may be caused by trauma, disease, or age. The cataractous lens obstructs the passage of light and tends to prevent the formation of a clear image on the retina.

Surgery currently is the only method of restoring vision in a patient blinded by cataracts. The surgical removal of the opacified lens becomes necessary when visual loss due to a cataract becomes significant. The lost optical power is typically restored by implantation of an artificial intraocular lens.

The cataract has become one of the most significant and common causes of ocular disability and blindness in our aging population. Cataract procedures are currently the most frequent surgery performed for a person over the age of 65. There were 4 million (U.S.: 1.6 million; foreign: 2.4 million) cataract surgeries performed in 1991, a number which is growing at an annual rate of 5%.

The classic method of cataract surgery is the removal of the intact lens through a 7–10 mm incision and its replacement with an intraocular lens made from bio-compatible polymers. This extracapsular cataract procedure restores vision but often causes post-operative complications resulting from the large incision, which include a prolonged healing process, increased trauma, and astigmatism. Nevertheless, about half of the current cataract procedures in the U.S. are performed using this extracapsular technique for removal of the intact lens.

More recently phacoemulsification devices, relying upon ultrasound, have been used for emulsifying the lens and removing it through a 3–5 mm incision in a shorter operative time. This technique provides easier rehabilitation and eliminates most of the post-operative complications resulting from the larger incision of conventional extracapsular cataract procedures.

For the phacoemulsification procedure, a 3–5 mm limbal or corneal incision is made allowing insertion of the instrument's tip into the anterior chamber in a direction almost parallel to the iris. Once the incision has been made, the central part of the anterior lens capsule must be widely opened to facilitate emulsification of the lens nucleus and cortical clean-up, as well as to provide for an ideal intraocular lens placement in the sulcus of the posterior chamber.

Phacoemulsification can be performed in the anterior chamber or posterior chamber of the eye. In the case of anterior chamber phacoemulsification, the cataract lens is maneuvered into the anterior chamber where it is carved and removed from the chamber. Anterior chamber phacoemulsification is more traumatic to the endothelial layer of the cornea than posterior chamber phacoemulsification, but it is often an easier procedure for the surgeon to perform. Posterior chamber phacoemulsification consists of carving or shaving the central part of the lens while the lens is still in the lens capsule. This method is more difficult to perform due to the possibility of rupturing the posterior lens capsule and exposing the vitreous humor which fills the volume of the inner eyeball.

When compared to conventional extracapsular cataract removal procedures, the phacoemulsification technique provides the advantages of a smaller incision, a stronger post-operative globe which reduces astigmatism, better wound closure, lower trauma and quicker improvement in vision. However, the phacoemulsification procedure is contraindicated in patients having a dislocated cataract lens, a shallow anterior chamber, miotic pupils, low cornea-endothelial cell counts, or myope (a totally hard lens). The phacoemulsification technique also requires intense training in maneuvering the ultrasonic probe to carve the cataract lens nucleus. The stray ultrasound energy can be destructive to the endothelial cells of the cornea ultimately resulting in complete degeneration. Due to these adverse circumstances, only about half of the U.S. surgeons currently prefer to use this phacoemulsification method over the conventional extracapsular method for cataract removal.

Use of phacoemulsification devices to perform endocapsular cataract removal has also been investigated. In such a procedure, the cataractous lens must be carved away while both the anterior and posterior sides of the lens capsule are left intact. The extreme difficulty associated with this procedure has limited its adoption so that only about 1% of the U.S. cataract removal procedures are performed using this endocapsular technique.

In addition to the above-described phacoemulsification devices, the prior art has included the motor driven cutting instrument, for reducing and removing a cataract-affected lens, as described in U.S. Pat. No. 4,368,734 (Banko) entitled SURGICAL INSTRUMENT issued Jan. 18, 1983. The instrument described in U.S. Pat. No. 4,368,734 is purportedly insertable into the lens capsule and usable to crush and sever the cataract-affected lens. The surgical instrument described in U.S. Pat. No. 4,368,734 includes a gripping implement (e.g., a hook) which is located opposite the cutting element of the instrument for purposes of gripping the material or object (e.g., ophthalmic lens) to be removed. Suction and irrigation lumens are incorporated into the instrument for removing the reduced lens material from the interior of the lens capsule.

Currently, there remains a need for the development of new ophthalmic lens removal apparatus capable of accomplishing endocapsular lens removal in a manner which is less time consuming, less skill intensive and associated with a minimal risk of iatrogenic damage to the posterior lens capsule.

SUMMARY OF THE INVENTION

The present invention comprises improvements and modifications to the rotary ophthalmic lens removal device described in parent application Ser. No. 07/984,229, of which this application is a continuation-in-part.

In general, the device described in parent application Ser. No. 07/984,229 is a rotary lens-reducing device comprising a handpiece having an elongate probe extending distally from the handpiece. An elongate rotatable drive shaft passes longitudinally through the probe and terminates, at its distal end, in a lens-reducing head. A protective tubular sheath is disposed about the rotatable shaft. The rotatable shaft and/or the sheath are axially movable so as to allow the lens-reducing head to be alternately deployed in a) a first non-operative position wherein the lens-reducing head is fully located within the inner bore of the tubular sheath so as to be shielded during insertion and retraction of the instrument or b) a second operative position wherein the lens-reducing head is advanced out of the distal end of the sheath so as to contact and reduce lens material. The lens-reducing head is specifically configured such that rotation of the head will create and sustain a forced circulation of fluid within the lens capsule. Such forced circulation within the lens capsule causes the ophthalmic lens to be pulled or drawn into contact with the rotating lens-reducing head, without the need for significant axial movement or manipulation of the probe while the lens-reducing head is rotating. The ability of the device to accomplish complete reduction of the ophthalmic lens, without requiring significant axial movement or manipulation of the probe concurrently with rotation of the lens-reducing head, serves to minimize the chance of iatrogenic perforation of the posterior lens capsule during the procedure.

Also, the preferred device described in parent application Ser. No. 07/984,229 incorporates a single passageway which extends longitudinally through the probe, and which may be alternately used for infusion of irrigation fluid into the lens capsule and aspiration of fluid/debris from the lens capsule.

The modifications and improvements which distinguish the present invention over that which was specifically described in parent application Ser. No. 07/984,229 include the following:

The provision of a modified protective tubular sheath having a distal end which is tapered, beveled or of otherwise non-symmetrical configuration such that a portion of the sheath continues to cover or shield a portion (e.g., one side) of the lens-reducing head, even while the lens-reducing head is located in its "operative" position. By such arrangement, the non-symmetric distal tip of the protective sheath serves to shield a portion (e.g., one side) of the rotating lens-reducing head during use, thereby preventing the lens-reducing head from inadvertently perforating the portions of the lens capsule which are located adjacent the protected portion (e.g., one side) of the lens-reducing head. Additionally such non-symmetric configuration of the distal tip of the protective sheath can function to direct the flow of fluid which is discharged from the rotating lens-reducing head in a direction away from the adjacent wall of the lens capsule thereby minimizing the severity or force with which the fluid impinges against the lens capsule. Furthermore such asymmetric configuration of the distal tip of the sheath can provide a sealing surface which contacts the surrounding puncture opening or incision in the lens capsule, thereby facilitating operation of the instrument with only minimal insertion of the sheath into the lens capsule, the opening in the lens capsule being of a generally oblong shape due to the angled insertion of the instrument. Also, the configuration of the distal portion of the sheath is preferably capable of skewing or deflecting the forced circulation of fluid which is created by rotation of the lens-reducing head. Such skewing or deflection of the flow enhances the ability of the device to set up a desired forced circulation of fluid around the periphery of the lens capsule, when the probe is maintained in a preferred position therewithin. Such directing or channeling of the forced circulation around the outer periphery of the fluid within the lens capsule facilitates rapid and complete reduction of the entire lens, without any significant requisite movement or manipulation of the probe. Furthermore, such directing or channeling of the forced circulation around the outer periphery of the lens capsule may optimize the efficiency of the lens-reduction procedure because such peripheral flow path is consistent with the anatomical configuration of the lens capsule, and the fact that the lens itself is usually made up of relatively hard material in its center with softer material around the periphery thereof.

The provision of separate fluid infusion and fluid/debris aspiration pathways extending longitudinally through the probe, such that irrigation fluid may be infused into the lens capsule concurrently with the aspiration of fluid/debris therefrom, or at least without the required interruption of one such procedure to permit accomplishment of the other, as is required with the single infusion/aspiration pathway incorporated in the preferred device described in parent application Ser. No. 07/984,229.

The provision of a specific embodiment of the invention wherein the probe portion of the instrument is of a curved configuration, rather than a straight configuration.

Further objects and advantages of the present invention, as well as the specific manner in which the modifications and improvements of the present invention interact with the basic elements of the device as described in parent application Ser. No. 07/984,229, will become apparent upon reading and understanding of the following detailed description and the accompanying drawings.

BRIEF DESCRIPTION OF THE DRAWINGS

FIG. 4 is a longitudinal sectional view of a portion of the rotary ophthalmic lens removal device of the present invention.

FIG. 4c is an enlarged longitudinal sectional view of the distal end of a modified embodiment of the probe shown in FIG. 4.

FIG. 4d is an enlarged perspective view of the rotary lens-reducing head of the device shown in FIG. 4.

Figure 4A:
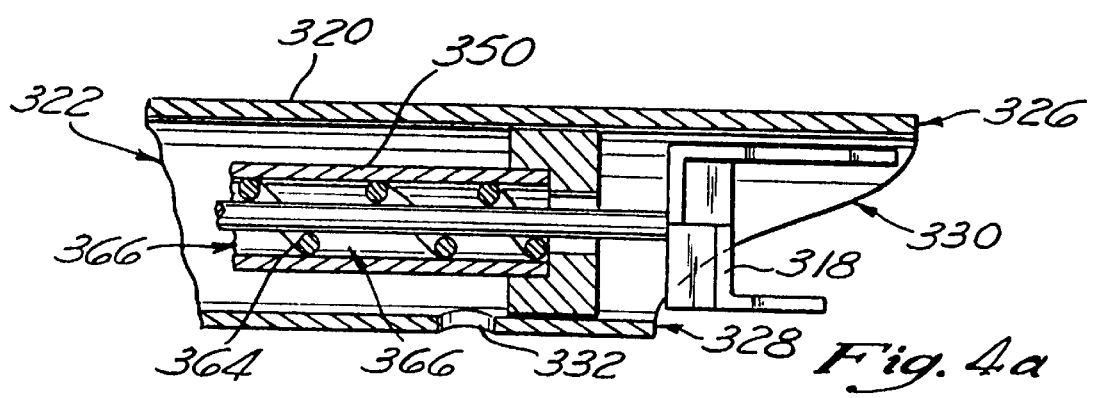
FIG. 4a is an enlarged longitudinal sectional view of the distal end of the probe portion of the device of FIG. 4 wherein the protective sheath positioned in its "operative" position relative to the rotatable lens-reducing head of the device.
Figure 4B:
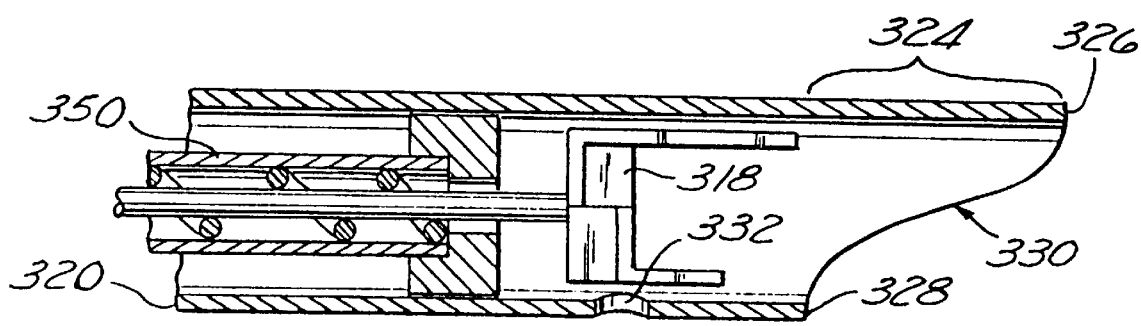
FIG. 4b is an enlarged longitudinal sectional view of the distal end of the probe portion of the device of FIG. 4 wherein the protective sheath is positioned in its protective or first "non-operative" position relative to the rotatable lens-reducing head of the device.
Figure 5A:
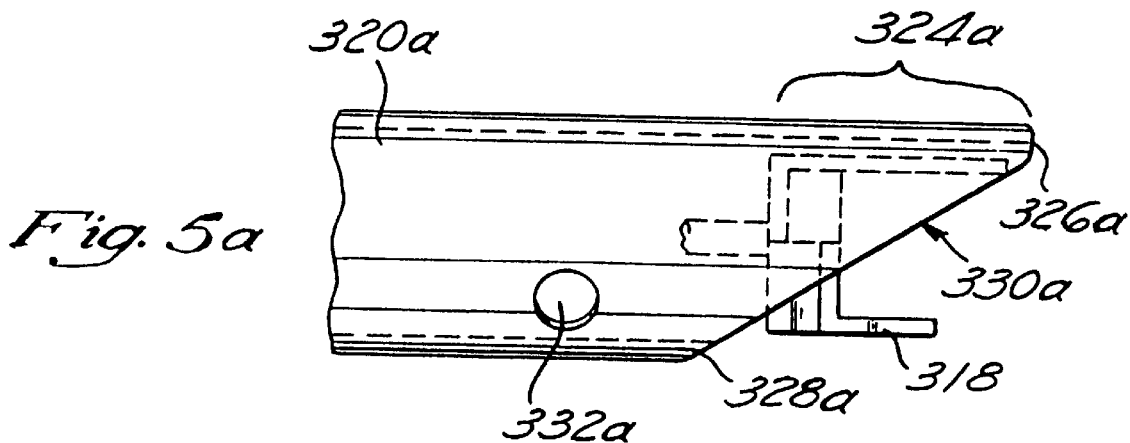

FIG. 5a is an enlarged elevational view of an alternative distal tip configuration for the probe portion of the device of FIG. 4.

Figure 5B:
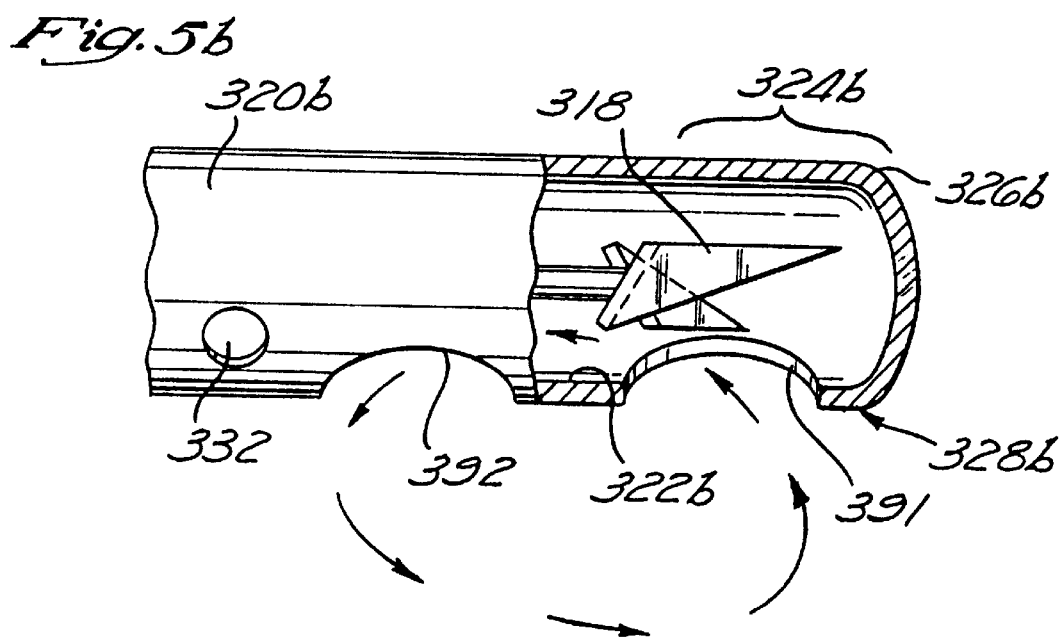

FIG. 5b is an enlarged elevational/cut-away view of an alternative distal tip configuration for the probe portion of the device of FIG. 4.

Figure 5C:
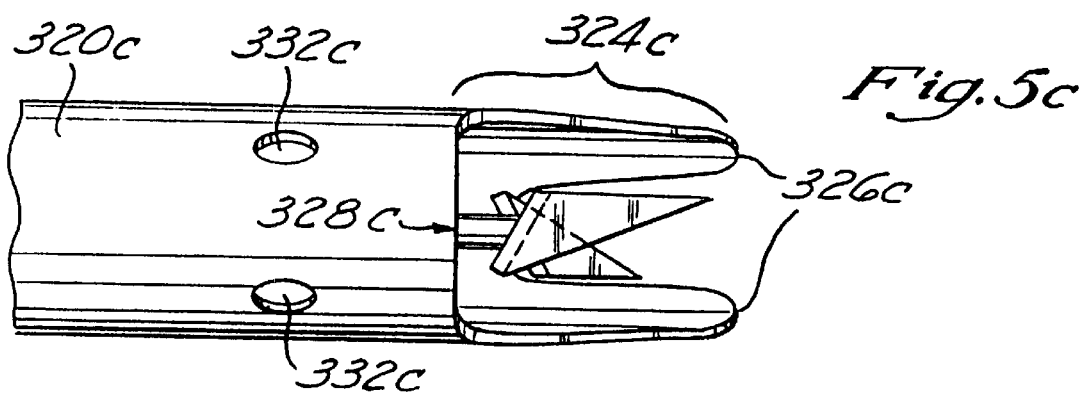

FIG. 5c is an enlarged bottom view of an alternative distal tip configuration for the probe portion of the device of FIG. 4.

FIG. 5d is an enlarged bottom view of an alternative distal tip configuration for the probe portion of the device of FIG. 4.

FIG. 6a is a longitudinal sectional view of a human eye into which the probe portion of a rotary ophthalmic lens removal device of the present invention has been inserted.

FIG. 6b is a frontal view of a human eye wherein a rotary ophthalmic lens removal device of the present invention has been inserted.

FIG. 7a is an elevational view of the distal end of the probe portion of the preferred embodiment of the ophthalmic lens removal device described in parent application Ser. No. 07/984,229.

FIG. 7b is an elevational view of the distal end of the probe portion of the preferred embodiment of the rotary ophthalmic lens device of the present invention.

FIG. 8a is an elevational view of a portion of an alternative embodiment of the rotary ophthalmic lens removal device of the present invention wherein the probe portion of the device is of a curved configuration, and wherein the protective sheath is positioned in its "operative" position relative to the rotatable lens-reducing head of the device.

FIG. 8b is an elevation view of a portion of an alternative embodiment of the rotary ophthalmic lens removal device of the present invention wherein the probe portion of the device is of a curved configuration, and wherein the protective sheath is positioned in its "non-operative" position relative to the rotatable lens-reducing head of the device.

FIG. 8c is an enlarged view of segment "C" of FIG. 8a.

DETAILED DESCRIPTION OF PREFERRED EMBODIMENTS

The following detailed description and the accompanying drawings are provided for purposes of describing and illustrating presently preferred embodiments of the invention only, and are not intended to limit the scope of the invention in any way.

It is to be appreciated that the invention described and claimed herein is a modification of the device which was previously described in Parent application Ser. No. 07/984,229. As such, the device described and claimed in this Continuation-In-Part Application incorporates many of the same structural and functional elements as the device previously described in Parent application Ser. No. 07/984,229.

The following detailed description is intended to focus only on those structural and functional elements of the present invention which are different from, or which add to, the elements of the invention already described in Parent application Ser. No. 07/984,229. Thus, because the entire disclosure of Ser. No. 07/984,229 is expressly incorporated herein by reference, the following paragraphs will not endeavor to fully redescribe each and every structural and functional element which the device the present invention shares in common with the device previously described in Parent application Ser. No. 07/984,229. Furthermore, it is to be recognized that the terminology used herein to refer to components of the invention may differ from the terminology used in the parent application Ser. No. 07/984,229 without necessarily indicating any structural or functional difference between the component referred to herein and a corresponding component referred to in the parent application.

Figure 1:
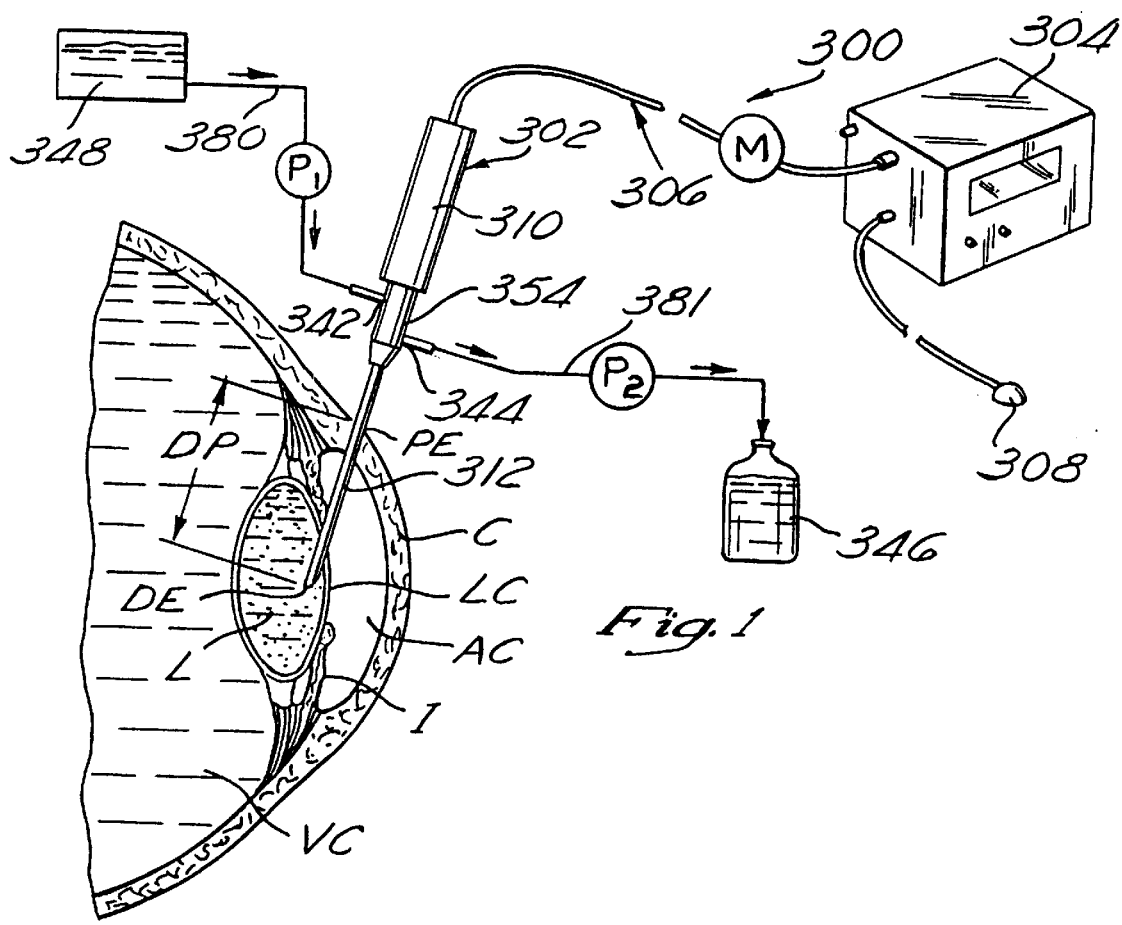
FIG. 1 is a schematic showing of a rotary ophthalmic lens removal system of the present invention along with a longitudinal sectional view of a human eye.

FIGS. 1 and 6 of this application contain illustrations of the human eye. The anatomical structures of the eye, shown in these figures, are labeled in accordance with the following legend:

| Cornea | C |
|---|---|
| Anterior Chamber | AC |
| Iris | I |
| Lens Capsule | LC |
| Lens | L |
| Vitreous Chamber | VC |

An Ophthalmic Lens Removal System

Figure 2:
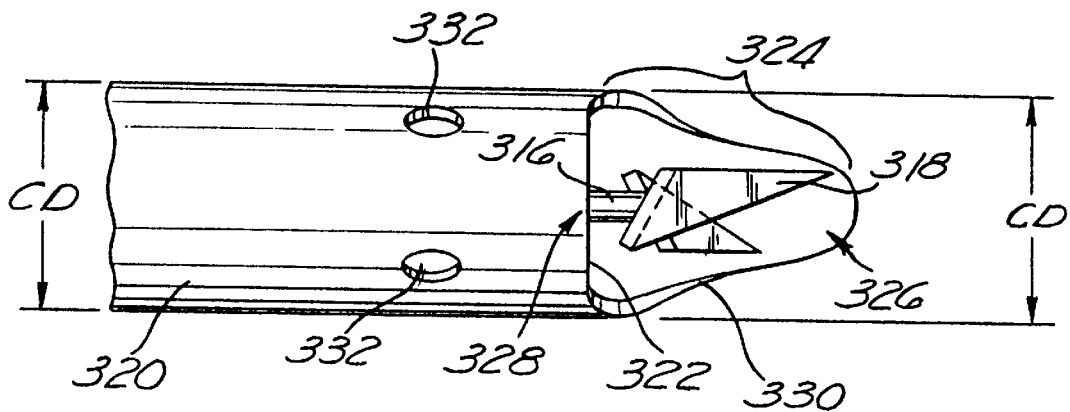
FIG. 2 is an enlarged perspective view of the distal end of the probe portion of the ophthalmic lens removal device shown in FIG. 1.

As shown in FIGS. 1–2, the system 300 of the present invention generally comprises a handpiece/probe device 302 which is connected to a motor-drive console 304 by way of a rotatable drive cable assembly 306. In the preferred embodiment a proportional or rheostatic control pedal 308 is connected to the motor-drive console 304 to facilitate foot-induced actuation/deactuation, and speed control, of the rotatable drive cable within the drive cable assembly 306 by the operator. One or more additional switches or control pedals (not shown) may also be provided for triggering and controlling the infusion and/or aspiration pumps $P_1$ and $P_2$ to facilitate infusion of fluid and/or aspiration of fluid and/or debris through the handpiece/probe device 302, as more fully described herebelow.

The handpiece/probe device 302 is preferably configured to include a proximal handpiece portion 310, a distal housing portion 354 and an elongate probe portion 312. The proximal handpiece portion 310 is sized and configured to be grasped and held by the human hand. The distal housing portion 354 is smaller in diameter than the proximal handpiece portion 310 (of 302) and extends from of the distal end of the handpiece portion 310 (of 302), as shown. The elongate probe portion 312 is an elongate member which is sufficiently small in diameter to be inserted into the mammalian eye, through a small incision or puncture opening.

Sectional showings of the internal components and construction of the distal housing portion 354 and elongate probe portion 312 are provided in FIGS. 4–4c. With specific reference to FIGS. 4–4d, the distal housing portion 354 is preferably configured to define therewithin a hollow inner chamber 370. A drive member 371 is coupled to the rotatable drive cable within the drive cable assembly 306 and extends into the hollow inner chamber 370, as shown. A rotatable drive shaft 316 is rotatably connected or engaged to the drive member 371, such that the shaft 316 may be thereby rotatably driven at speeds required for the lens reduction procedure (e.g., 50,000–150,000 rpm). In the embodiment shown, the rotatable drive shaft 316 is inserted into a bore formed in the distal face of the drive member 371.

A seal (rotating face) 373 is positioned about the outer surface of the drive member 371, in engagement with the adjacent wall of the hollow inner chamber 370 to prevent seepage or leakage of liquid from the hollow inner chamber 370 into the interior of the proximal hand piece portion 310 (of 302). In the preferred embodiment, the seal 373 comprises a rotating face seal which is mounted about the outer surface of the drive member 371, and which incorporates a pliable flange portion which seats against and rides upon the adjacent wall or bulkhead 358 of the hollow inner chamber 370, thereby forming the desired seal 373 of the hollow inner chamber 370.

The elongate probe portion 312 extends in the distal direction from the distal housing portion 354. As shown, the elongate probe portion 312 comprises an axially movable outer sheath 320 which has a hollow bore or lumen 322. A non-rotatable rigid sleeve 350, having a hollow bore or lumen 366, is coaxially centered within the hollow bore or lumen 322 of the rigid sleeve 350 and extends longitudinally therethrough. The rotatable drive shaft 316 passes longitudinally through the hollow bore or lumen 366 of the rigid sleeve 350, and is surrounded by a helical bearing member 364, such as a helical coil of smooth stainless steel wire. Such helical bearing member 364 abuts concurrently against the outer surface of the rotatable drive shaft 316, and the inner luminal surface of the surrounding rigid sleeve 350. Thus, the helical bearing member 364 serves to rotatably support the rotatable drive shaft 316 in a coaxially centered position within the hollow bore or lumen 366 of the rigid sleeve 350. A transverse bulkhead 358 is formed within the hollow bore or lumen 322 of the axially movable outer sheath 320, near the distal end thereof. The distal end of the non-rotatable rigid sleeve 350 is in abutment with and is supported by bulkhead 358, as shown. Thus, the distal end of the rigid sleeve 350 is maintained in a coaxially centered position within the hollow bore or lumen 322 of the axially movable outer sheath 320. A central aperture 360 extends longitudinally through bulkhead 358, in alignment with the hollow bore or lumen 366 of the rigid sleeve 350. The rotatable drive shaft 316 extends longitudinally beyond the distal end of the rigid sleeve 350, and through the central aperture 360 of bulkhead 358, as shown. In the particular embodiment shown in FIGS. 4, 4*a* and 4*b* the central aperture 360 of the bulkhead 358 is larger than the outer diameter of the rotatable drive shaft 316 or otherwise configured to permit infusion fluid to flow from the inner hollow bore or lumen 366 of the non-rotatable rigid sleeve 350, through central aperture 360, and out of the open distal end 324 of the axially movable outer sheath 320. Thus, the bulkhead 358 and its central aperture 360 provide a centering support for the rotatable drive shaft 316 as well as a fluid pathway parallel to the rotatable drive shaft 316 and a barrier to prevent backflow of fluid into the space of the hollow bore or lumen 322 between the inner surface of the sheath 320 and the outer surface if the sleeve 350.

In one alternative embodiment shown specifically in FIG. 4*c*, the drive shaft 316*a* is truncated such that its distal end terminates proximal to the bulkhead 358*a*. A tubular extension member 420 is mounted on the distal end of the rotatable drive shaft 316*a*. Such tubular extension member 420 extends through the central aperture 360*a* formed in bulkhead 358*a*. The central aperture 360*a* is substantially the same size as the outer surface of the tubular extension member 420, thereby forming a simple sleeve bearing which allows free rotation of the tubular extension member 420. A hollow flow passageway 422 extends longitudinally through the tubular extension member 420. Inflow apertures 424 are formed in the tubular extension member 420 proximal to the bulkhead 358*a*. Such inflow apertures 424 are in fluidic communication with the hollow bore or lumen 366 of the rigid sleeve 350. Outflow apertures 426 are formed in the distal portion of the tubular extension member 420, distal to the bulkhead 358*a*. By such arrangement, a flow of irrigation fluid may be infused through fluid inlet tube 380 through hollow inner chamber 370, through the hollow bore or lumen 366 of the rigid sleeve 350, through inflow apertures 424, through the internal hollow flow passageway 422 of tubular extension member 420, and out of outflow apertures 426. Thus, in this embodiment, the bulkhead 358*a* functions dually as a barrier to prevent backflow into the space of the hollow bore or lumen 322 between the inner surface of the axially movable outer sheath 320 and the outer surface of the rigid sleeve 350 and as a centering support for the tubular extension member 420 and thereby for the rotatable drive shaft 316 which permits operative rotation of the tubular extension member 420 within its central aperture 360*a*. A fluid pathway is independently established by the internal hollow flow passageway 422.

In the particular embodiment shown, the axially movable outer sheath 320 is longitudinally shiftable, back and forth, relative to the stationarally positioned non-rotatable rigid sleeve 350, bulkhead 358, rotatable drive shaft 316 and distal lens-reducing head 318. This allows the axially moveable outer sheath 320 to be volitionally shifted back and forth between an exposed "operative" position wherein the lens-reducing head 318 is sufficiently exposed to perform its intended lens-reducing function, and a shielded "non-operative" position wherein the axially movable outer sheath 320 is moved distally to a point where the entire lens-reducing head 318 is disposed within the hollow bore or lumen of the axially moveable outer sheath 320. In the embodiment shown, the longitudinal movement of the axially movable outer sheath 320 is facilitated by anchoring of the axially movable outer sheath 320 to a distal segment 354*b* of the distal housing portion 354. The distal segment 354*b* of distal housing portion 354 is slidably advanceable and retractable over the proximal segment 354*a* thereof. Spring loaded engagement ball members 357 are seatable in alternate grooves or detents 359 to hold the axially movable outer sheath 320 and distal segment 354*b* of the distal housing portion 354 in either the exposed "operative" position or the shielded "non-operative" position. Accordingly, if it is desired to move the rotatable drive shaft 316 and distal segment 354*b* of the distal housing portion 354 from the second "operative" position to the first "non-operative" position, the operator will push or force the distal segment 354*b* of the distal housing portion 354 and axially moveable outer sheath 320 in the distal direction, causing spring loaded engagement ball members 357 to disengage from the "second" position grooves or detents 359*a*, and to move to a point where the spring loaded engagement ball members 357 will drop into and frictionally engage the "first" position grooves or detents 359*b*. Thus, the distal segment 354*b* of the distal housing portion 354 and axially moveable outer sheath 320 will be frictionally held and maintained in the first "non-operative" position until such time as the operator volitionally moves the distal segment 354*b* of the distal housing portion 354 and axially moveable outer sheath 320 back to their second "operative" position.

Although, as described hereabove, the embodiment shown in the drawings utilizes an axially moveable outer sheath 320 which is axially moveable back and forth between the first "non-operative" and second "operative" positions, it will be appreciated that, as an alternative, the axially moveable outer sheath 320 may be maintained in an axially stationary position, and the rotatable drive shaft 316, bulkhead 358 and lens-reducing head 318 may be rendered movable or shiftable, back and forth, to achieve the intended alternate positioning of the lens-reducing head 318 in the first "non-operative" and second "operative" positions relative to the axially moveable outer sheath 320.

Modified Distal Tip

In some embodiments of the invention, the axially moveable outer sheath 320 may also be rotatable about its longitudinal axis so as to facilitate rotational repositioning of the distal end 324 of the axially moveable outer sheath 320 after it has been inserted into the eye, thereby eliminating the need to rotate the entire device. This aspect of the invention is particularly useful in combination with the modified configuration of the distal end 324 of the sheath as described more fully herebelow.

In accordance with the present invention, the distal end 324 of the axially moveable outer sheath 320 is specifically configured such that, even when the lens-reducing head 318 is deployed in its "operative" location relative to the axially moveable outer sheath 320, a portion (e.g., one side) of the lens-reducing head 318 will remain shielded or protected by an axial protruding portion (e.g., one side) of the axially moveable outer sheath 320. Such modified configuration of the distal end 324 of the axially moveable outer sheath 320 serves the dual functions of a) protecting against inadvertent puncture of or damage to the lens capsule LC, and b) directing or channeling the forced circulation flow of fluid induced by the lens-reducing head 318 within the lens capsule LC so as to improve the efficiency of the lens-reduction procedure.

Referring specifically to the embodiment shown in FIGS. 2 and 4–4c, the distal end 324 of the axially moveable outer sheath 320 is preferably configured such that protruding side 326 of the axially moveable outer sheath 320 extends beyond the non-protruding side 328 of the axially moveable outer sheath 320. A diagonal or curved transverse surface 330 transverses from the distal end of the protruding side 326 to the distal end of the non-protruding side 328. Thus, when the lens-reducing head 318 is located in its second "operative" position, as shown in FIG. 4a, the side of the lens-reducing head 318 next to the non-protruding side 328 of the distal end 324 of axially moveable outer sheath 320 is sufficiently exposed to perform its intended lens-reducing function, while the other side of the lens-reducing head 318 next to the protruding side 326 of the distal tip 324 of the axially moveable outer sheath 320 is protected from contacting adjacent anatomical structures. As such, the protruding side 326 of the distal end 324 of the axially moveable outer sheath 320 will prevent or deter that side of the lens-reducing head 318 from inadvertently contacting or perforating the adjacent lens capsule LC (i.e., that portion of the lens capsule LC which is next to that side of the axially moveable outer sheath 320). This lateral shielding function of the protruding side 326 of the distal end 324 is particularly advantageous when the axially moveable outer sheath 320 is rotated, following its insertion into the lens capsule LC, to an orientation whereby the protruding side 326 of the axially moveable outer sheath 320 is next to the closest wall or potion of the lens capsule LC and the non-protruding side 328 is directed toward the center of the lens capsule LC.

Although the configuration of the distal end 324 shown in FIGS. 2 and 4 is a presently preferred configuration, it will be appreciated that various alternative configurations of the distal end 324, such as those shown in FIGS. 5a–5c, may also achieve the intended functions of this aspect of the invention.

FIG. 5a shows a first alternative configuration for the distal end 324a of the protective axially moveable outer sheath 320a, wherein a straight angle-cut cross sectional transverse surface 330a extends between the protruding side 326a of the axially moveable outer sheath 320a and the non-protruding side 328a thereof. Thus, the modified configuration shown in FIG. 5a differs from the preferred configuration shown in FIG. 2 by replacement of the curved transverse surface 330 (FIG. 2) with a substantially straight angle-cut transverse surface 330a (FIG. 5a).

Another alternative configuration is shown in FIG. 5b, wherein the distal end 324b of the axially moveable outer sheath 320b comprises a blunt-tipped closed-ended tube with appropriately positioned inlet and outlet apertures 391, 392 formed therein, as shown in FIG. 5b. The lens-reducing head 318, when in its second or "operative" position, is disposed immediately adjacent the inlet aperture 391 such that the blades of the lens-reducing head 318 will pass or extend partially or fully through the inlet aperture 371 so as to come into contact with, and reduce, any lens L matter which is drawn into or otherwise positioned within or immediately next to the inlet aperture 371. In this regard, the rotating lens-reducing head 318 is preferably configured and positioned to pull or draw fluid (and lens matter) inwardly through inlet aperture 391. The outlet aperture 392 permits fluid which has been drawn into the axially moveable outer sheath 320b, and any accompanying lens debris or fragments, to be expelled out of the hollow bore or lumen 322b of the axially moveable outer sheath 320b through the outlet aperture 392.

Such configurations of the axially moveable outer sheath 320 as depicted in FIG. 5b, are conceived to reduce the need for movement of the lens-reducing head 318 between an "operative" and "non-operative" position.

Another alternative configuration of the distal end 324c of the axially moveable outer sheath 320c is shown in FIG. 5c. In this alternative configuration, the non-protruding side 328c of the axially moveable outer sheath 320c is cut perpendicular to the longitudinal axis of the axially moveable outer sheath 320c, and the protruding side 326c is bifurcated or shaped to include multiple axial protrusion, at least one of which extends slightly beyond the distal most end of the lens-reducing head 318 when the lens-reducing head 318 is disposed in its second or "operative" position as shown.

The manner in which the modified tip portion 324 of the axially moveable outer sheath 320 operates to channel or direct fluid flow within the lens capsule LC, is specifically illustrated in FIGS. 7a and 7b. FIG. 7a shows an embodiment of the device wherein the axially moveable outer sheath 320 is cut straight across at its distal end, as described and shown in parent application Ser. No. 07/984,229. In such embodiment, the rotation of the lens-reducing head 318 causes a flow of fluid to be axially drawn toward the frontal or proximal aspect of the lens-reducing rotating head 318, and the resultant expulsion or exhaust of liquid is deflected radially outward by the straight-cut distal end of the axially moveable outer sheath 320, in multiple, axially symmetrical lateral directions, as indicated by the arrows shown on FIG. 7a.

FIG. 7b shows a modified device of the present invention wherein the axially moveable outer sheath 320 incorporates a distal end 324 wherein a first or shielded side 326 of the distal end 324 protrudes beyond the lens-reducing rotating head 318, while a second non-shielded side 328 of the distal end 324 terminates short of the rotating distal lens-reducing head 318. In this modified embodiment, the rotating distal lens-reducing head 318 draws fluid toward the frontal or distal aspect of the lens-reducing rotating head 318. Thereafter, fluid drawn into the rotating lens-reducing head 318 is deflected by the axially moveable outer sheath 320 and caused to be expelled or channeled away from the second shielded side 328 of the axially moveable outer sheath 320, as shown by arrows on FIG. 7b. In this manner, the modified configuration of the distal end 324 of the axially moveable outer sheath 320 serves to channel or direct the forced circulation of fluid toward one side (i.e., the second non-shielded side 328) of the axially moveable outer sheath 320. When appropriately positioned within the lens capsule, such directed or channeled flow of fluid may be specifically directed about the periphery of the lens capsule so as to optimize and facilitate rapid reduction of the entire lens L, without the need for any significant longitudinal axial manipulation or movement of the probe.

The ability of the present invention to channel or direct the fluid flow about the periphery of the lens capsule LC helps to optimize the speed and efficiency with which the ophthalmic lens L is reduced because the cortex or outer portion of the lens L is typically softer and more easily reducible than the nucleus or center portion thereof. In this regard, the channeling or directing of the flow of fluid about the periphery of the lens capsule LC, results in the soft outer cortical portion of the lens L being preferentially reduced and fluidized by the rotation of the lens-reducing head 318. As the outer cortical portion of the lens L is reduced the relatively hard central or cataract portion of the lens L begins to slowly and gently tumble or rotate within the lens capsule LC. The continued forced circulatory flow of fluid about the periphery of the capsule further facilitates such tumbling or rolling of the nucleus or cataract portion of the lens L, until reduction of the entire lens L has been accomplished. Thus, in this way, the channeling or directing of the fluid flow within the lens capsule by the modified distal end 324 of the axially moveable outer sheath 320 serves to optimize the speed and efficiency with which the ophthalmic lens L is reduced and removed.

Infusion/Aspiration Through the Probe

Additionally, as shown in FIGS. 4–4c, the handpiece/probe device 302 of the present invention preferably incorporates separate passageways for a) infusion of irrigation fluid into the interior of the lens capsule LC, and b) aspiration of fluid/debris from the interior of the lens capsule LC. Such separate passageways for irrigant infusion and fluid/debris aspiration are shown in FIGS. 4–4b. As shown, the sleeve 350 is concentrically positioned around the rotatable drive shaft 316, within the hollow bore or lumen 322 of the protective tubular sheath 320. The proximal end 352 of the rigid sleeve 350 is anchored to the distal housing portion 354a, while the distal end 356 of the rigid sleeve 350 is anchored to a bulkhead 358 positioned within the distal portion of the hollow bore or lumen 322 of the protective axially moveable outer sheath 320. A central aperture 360 extends longitudinally through bulkhead 358, and the rotatable drive shaft 316, which extends longitudinally through the hollow bore or lumen 366 of the rigid sleeve 350, passes through the central aperture 360 as shown. The helical bearing member 364 concurrently abuts against the inner surface of the hollow bore or lumen 366 of rigid sleeve 350 and against the outer surface of the rotatable drive shaft 316. Thus, the helical bearing member 364 serves to hold the rotatable drive shaft 316 in a coaxially centered position within the bore 366, while allowing the rotatable drive shaft 316 to rotate freely. The continuous helical or spiral space defined between the individual convolutions of the helical bearing member 364 forms a helical or spiral flow path through which irrigation fluid may be infused.

The hollow inner chamber 370 formed within the handpiece/probe device 302 is in fluidic communication with the irrigation fluid inlet port 342, and leads into the proximal end 352 of the bore 366 of the rigid sleeve 350. Seal 373 is configured and constructed to permit rapid rotation of the rotatable drive member 371, while preventing liquid from escaping from the hollow inner chamber 370 proximally along the drive member 371 and into other components within the proximal handpiece portion 310 of the handpiece/probe device 302. A pump or pressure source $P_1$, is applied to supply vessel 348 when it is desired to infuse fluid from the supply vessel 348, through the elongate probe portion 312. Thus, by actuating pump $P_1$, fluid may be infused through the irrigation fluid inlet port 342, through hollow inner chamber 370, and through the spiral gap or flow path created between the individual convolutions of the helical bearing member 364. As such, the infused fluid will reach the distal end 356 of the rigid sleeve 350, and will exit through central aperture 360 in bulkhead 358. Such fluid will subsequently pass out of the open distal end 324 of the protective axially moveable outer sheath 320.

The preferred handpiece/probe device 302 of the present invention also incorporates a separate aspiration passageway for aspirating reduced lens matter and/or other fluid or debris from the interior of the lens capsule LC. In the embodiment shown in FIG. 4, such aspiration pathway comprises the peripheral portion of the hollow bore or lumen 322 of the axially moveable outer sheath 320 which surrounds the outer surface of rigid sleeve 350. One or a plurality of fluid/debris inlet aperture(s) 332 are formed in the sidewall of the axially moveable outer sheath 320 near the distal end 324 thereof. In the preferred embodiment shown, the inlet apertures 332 are specifically positioned such that, when the axially moveable outer sheath 320 is in its second or "operative" position (FIG. 4a) relative to the rotating lens-reducing head 318, such fluid/debris inlet apertures 332 will be located behind or proximal to the bulkhead 358, thereby allowing fluid and/or debris to enter into the hollow bore or lumen 322 of axially moveable outer sheath 320 through inlet apertures 332. A fluid/debris outlet port 344 is formed in the rigid cylindrical distal housing portion 354b near the proximal end of the elongate probe portion 312 to facilitate the suctioning of fluid/debris, through the hollow lumen or bore 322 of the axially moveable outer sheath 320, and through aspiration tube 381, into collection vessel 346. A pump $P_2$ positioned between fluid debris outlet port 344 and collection vessel 346 may be utilized to facilitate such aspiration of fluid/debris through the probe.

Because the preferred handpiece/probe device 302 of the present invention incorporates separate fluid infusion and fluid/debris aspiration passageways, it is possible to infuse irrigation fluid into the lens capsule LC while concurrently aspirating lens L debris and/or fluid from the interior of the lens capsule LC. It is to be noted, however, that such concurrent infusion and aspiration are not required. In fact, irrigant fluid may be occasionally or periodically infused, at the will of the operator, and the fluid/debris may be occasionally or periodically aspirated, also at will. The infusion and aspiration processes may be wholly independent of each other. Furthermore, the independent processes of irrigation and/or aspiration may be performed simultaneous with the rotation of the lens-reducing head 318 or while the head 318 is in a non-rotating, stationary mode.

Also, it will be appreciated that the infusion and aspiration pathways may be reversed or interchanged by alternately connecting the aspiration tubing and aspiration pump $P_2$ to inlet port 342 and the infusion tubing and pump $P_1$ to the fluid/debris outlet port 344.

Although the embodiment shown in the drawings (FIG. 4) incorporates the inlet and outlet ports 342, 344, and their corresponding fluid inlet and outlet tubes 380, 381, on the distal housing portion 354 of the handpiece/probe 302, such inlet and outlet ports 342, 344 and corresponding fluid tubes 380, 381 may be alternately located elsewhere on the device, such as on the proximal end of the handpiece portion 310 of the handpiece/probe device 302. For example, the fluid infusion and withdrawal tubes could be connected to the rear or proximal end of the handpiece portion 310 of the handpiece/probe device 302, behind the operators hand, to prevent the tubes from interfering with viewing and/or manipulation of the elongate probe portion 312 by the operator, during use. In such arrangements, a fluid infusion tube or conduit and a fluid/debris aspiration tube or conduit will extend through the proximal handpiece portion 310 of the handpiece/probe device 302 to carry the respective fluid and/or debris through of the hollow inner chamber 370 formed within the distal housing portion 354.

Positioning and Operating the Probe

FIGS. 6a and 6b provide anatomical illustrations of the human eye, showing the preferred method of inserting and positioning the elongate probe portion 312 so as to minimize the likelihood of damage to the lens capsule LC, and to maximize the efficiency of the forced fluid circulation created by the rotating lens-reducing head 318.

Figure 3:
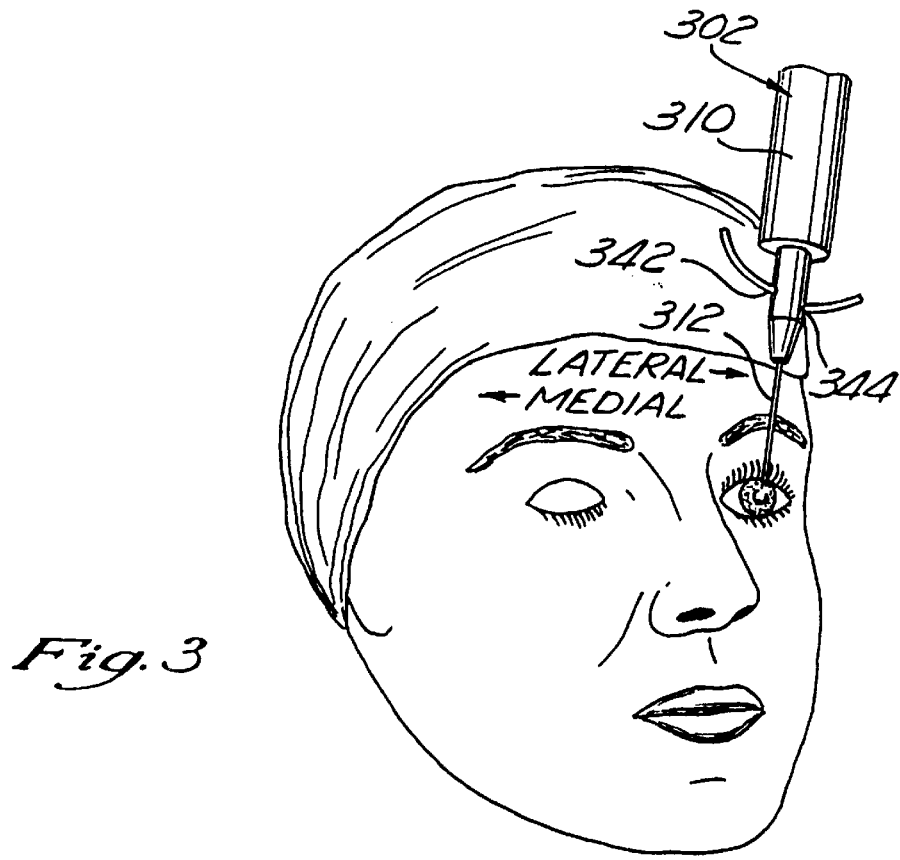
FIG. 3 is a perspective view of the device of FIG. 1 positioned for insertion into the eye of a human being.

As shown in FIG. 6a, the elongate probe portion 312 is preferably inserted into the lens capsule LC through a previously formed needle tract or incision. Such needle tract or incision forms a small first opening 400 in the cornea C shown at the twelve-o'clock position. An underlying second opening 402 is then formed, slightly to the medial side of center, in the anterior aspect of the lens capsule LC. The elongate probe portion 312 is advanced through the needle tract or incision, and through the corneal opening 400 and capsular opening 402 created thereby, such that the distal end 324 is inserted into the lens capsule LC and such that the distal end of the elongate probe portion 312 is angled inwardly toward the mid line of the body, and the proximal portion of the handpiece 310 is angled outwardly, away from the forehead of the patient. Such preferred angular positioning of the handpiece/probe 302 is shown in FIGS. 3 and 6a.

As shown in FIGS. 6a and 6b, the axially moveable outer sheath 320 may be rotated about its longitudinal axis to a preferred rotational orientation wherein the protruding side 326 of the axially moveable outer sheath 320 is adjacent to the closest wall or portion of the lens capsule LC and the non-protruding side 328 of the axially moveable outer sheath 320 is aimed or directed toward the lens-containing interior of the lens capsule LC. By such preferred positioning of the sheath 320, the forced circulation or flow induced by the rotating distal lens-reducing head 318, as illustrated in FIG. 7b, will flow around the periphery of the lens capsule LC to facilitate initial reduction of the cortex of the lens L followed by complete reduction of its nucleus, without the need for any significant axial (i.e., longitudinal) movement or manipulation of the elongate probe portion 312 within the lens capsule LC. As shown in FIG. 6a, elongate probe portion 312 is inserted into the lens capsule LC to a depth such that the aspiration inlet apertures 332 are located within the lens capsule LC. It is preferred to preferentially bias the location of the aspiration inlet apertures 332 toward the non-protruding side 328 of the elongate probe portion 312 in order to reduce the depth within the lens capsule LC to which the elongate probe portion 312 must be inserted axially such that inlet apertures 332 are within the bounds of the lens capsule LC.

After the elongate probe portion 312 has been inserted and the axially moveable outer sheath 320 rotated about its longitudinal axis to its desired orientation, the axially moveable outer sheath 320 is retracted such that the lens-reducing head 318 becomes relocated from its first shielded or "non-operative" position (FIG. 4b) to its second exposed or "operative" position (FIG. 4a). With the lens-reducing head 318 located in its second "operative" position (FIG. 4a), the proportional or rheostatic control pedal 308 is depressed so as to actuate a motor within the motor-drive console 304, thereby driving the rotatable drive shaft 316 and the lens-reducing head 318, via rotatable drive cable assembly 306 and drive member 371. In embodiments which incorporate a control pedal 308 having proportional or rheostatic capability for controlling the rotational speed of the handpiece/probe device 302, the operator may selectively control the degree to which the control pedal 308 is depressed, to adjust the rotational speed of the rotatable drive shaft 316 and lens-reducing head 318.

The ophthalmic lens L is initially in the form of a substantially solid mass, within the interior of the lens capsule LC. The periphery or outer cortex portion of the lens L is typically softer than the center or nucleus thereof. Thus, when the elongate probe portion 312 is properly positioned, the soft outer cortical portion of the lens L is preferentially reduced and fluidized by rotation of the lens-reducing head 318. The directed fluid flow created by the device (see FIG. 7b) will preferentially circulate around the periphery of the lens capsule LC so as to cause the lens L to begin a flat spin within the lens capsule LC. Such initial spinning of the lens L will cause the soft outer periphery of the lens L to be further reduced (e.g., slurried or liquified), thereby decreasing the overall size of the remaining lens L to a point where it begins to tumble and roll within the lens capsule LC. As the remaining lens L tumbles, it is repeatedly drawn into contact with the lens-reducing head 318. As a result, the relatively hard nucleus portion of the lens L will be reduced thereby accomplishing complete reduction of the lens L, without the need for any significant axial (i.e., longitudinal) movement of the elongate probe portion 312 within the lens capsule LC.

During or after reduction of the lens L, the aspiration pump $P_2$ may be utilized to draw lens L fragments and accompanying fluidic debris from the interior of the lens capsule LC, into aspiration inlet apertures 332, through the aspiration passageway existing within the hollow bore or lumen 322 of the axially moveable outer sheath 320, and out of the aspiration port 344, such that the debris and accompanying fluid may be collected in a fluid/debris collection vessel 346. Simultaneously or separately clear make up fluid, such as 0.9% NaCl solution, may be pumped, by pump $P_1$, through fluid inlet tube 380, through fluid inlet port 342, through hollow inner chamber 370, through lumen 366, through central aperture 360, and out of the distal end opening of the sheath 320, thereby replacing the debris/fluid aspirated from the interior of the lens capsule LC with clear make-up liquid. The viscosity and other fluidic properties of the make-up liquid may be varied to manipulate the forced circulation of fluid induced by rotation of lens-reducing head 318 to enhance reduction of the lens L.

After the lens L fragments and debris have been removed and replaced with clear liquid or other lens L replacement material, the elongate probe portion 312 may be extracted from the interior of the capsule LC and removed.

Thereafter, the needle tract or incision openings 400, 402 in the cornea and lens capsule respectively through which the elongate probe portion 312 was inserted may be closed by appropriate closure means or an appropriate lens L implant introducer may be immediately inserted through the same needle tract or incision openings 400, 402, or by way of a separately formed tract or incision, so as to implant a prosthetic replacement lens L within the interior lens capsule LC. Although the twelve-o'clock entry position has been described for illustrative purposes, the above methodologies are not restricted to use of the twelve-o'clock position, but can be utilized with other entry positions such as the nine-o'clock position.

The lens-reducing head 318 is specifically configured and constructed to include impeller members 319 which, when rotated, create an axial flow of fluid toward the distal or frontal aspect of the lens-reducing head 318, as shown in FIG. 7b. For embodiments having the lens-reducing head 318 shown in the figures, the presently preferred rotational speed of the lens-reducing head 318 will be 50,000–150,000 rpm. It will be appreciated, however, that the optimal rotational speed of the lens-reducing head 318 will be determined by a number of factors, including the specific size and configuration of the lens-reducing head 318 as well as considerations relating to the optimization of the resultant induced forced circulation of fluid which is created by the rotation of the drive shaft 316 and lens-reducing head 318 of the device. Accordingly, any suitable rotational speed may be employed based on the specific structural attributes of the device and the physical effects created by rotation of the drive shaft 316 and lens-reducing head 318.

Pumping/Non-Pumping Effects of the Rotating Assembly

In the embodiments shown, the rotation of the drive shaft 316 may operate to propel or pump liquid through the helical or spiral flow path defined between the individual convolutions of the helical bearing member 364. In this regard, when the drive shaft 316 is rotated in a clock-wise direction, the rotating outer surface of the drive shaft 316 will frictionally propel liquid in the distal direction, through the spiral flow path defined by the convolutions of the helical bearing member 364. This will result in some pumping or propulsion of liquid through the bore 366 of the rigid sleeve 350. This pumping effect created by the rotating drive shaft 316 may be utilized as means for enhancing or controlling the infusion of a fluid (e.g., an irrigant solution) through bore 366 and into the eye. Alternatively, in some embodiments of the intention, it may be desirable to nullify or prevent such pumping action of the rotating drive shaft 316. One means of nullifying or preventing such pumping action is to divide the helical bearing member 364 into a plurality of oppositely wound segments or regions. In this regard, each oppositely wound segment or region of the helical bearing member 364 will create opposite fluid flow forces within the bore 366 as the drive shaft 316 rotates. Such opposite fluid flow forces created by the oppositely wound segments or regions of the bearing member 364 may be intensity-matched to offset or cancel one another, thereby resulting in effective cancellation of any fluid pumping effect created by rotation of the drive shaft 316.

It will be appreciated that this aspect of the invention may be purposely utilized to effect or control pumping or non-pumping of fluid into the eye during a lens removal procedure using the device of the present invention.

Curved Embodiments of the Probe

FIGS. 8a–8c show an alternative embodiment of the invention wherein a handpiece/probe device 302d has an elongate probe portion 312d which is of curved configuration. In this embodiment, the axially moveable outer sheath 320d of the elongate probe portion 312d has a distal end 324d of a configuration substantially the same as that shown in FIG. 2. The protruding side 326d of the distal end 324d is laterally opposite the non-protruding side 328d thereof. The distal housing portion 354d and sheath 320d are alternately shiftable back and forth between a second "operative" position (FIG. 8a) and a first "non-operative" position (FIG. 8b). In this regard, when the distal housing portion 354d and axially moveable outer sheath 320d are retracted to their fully proximal position as shown in FIG. 8a, the lens-reducing head 318d of the device will protrude out of the open distal end of the sheath, but will remain partially shielded on one side by the protruding side 326d of the distal end 324d of the axially moveable outer sheath 320d as described hereabove with respect to the embodiment shown in FIGS. 1–2. Alternatively, when the distal housing portion 354d and axially moveable outer sheath 320d are advanced to their fully distal position, the lens-reducing head 318d will be retracted into the lumen of the axially moveable outer sheath 320d, as shown in FIG. 8b.

As shown in FIG. 8c, the curved embodiment of the elongate probe portion 312d differs from the above-described preferred embodiment shown in FIGS. 1–4 in that a helical spacing member 490 is disposed between the outer surface of the rigid sleeve 350d and the inner surface of the surrounding axially moveable outer sheath 320d. This helical spacing member 490 may be formed of the same material as the helical bearing member 364d. The helical spacing member 490 is of a cross-sectional dimension or diameter which maintains the desired coaxial location of the rigid sleeve 350d in the surrounding axially moveable outer sheath 320d.

As described hereabove, the alternate positioning of the lens-reducing head 318 in the "operative" and "non-operative" positions may be achieved by either a) axially moving the lens-reducing head 318 relative to the sheath 320, or b) axially moving the sheath 320 relative to the lens-reducing head 318. In the curved embodiments shown in FIGS. 8a and 8b, this is accomplished by axially moving the sheath 320d, back and forth, as shown. It will be appreciated, that in order to accommodate such axial movement of the sheath 320, it will be necessary for one of the sheath 320 or sleeve 350 to be of rigid curved configuration while the other thereof is sufficiently pliable to accommodate such rigid curved configuration as the sheath 320 is moved back and forth between its "operative" position (FIG. 8a) and its "non-operative" position (FIG. 8b). Also, in such curved embodiments, it will be necessary for the drive shaft 315 to be sufficiently flexible to undergo rotation while maintained in the desired curved configuration.

For example, in the device shown in FIGS. 8a and 8b, the outer sheath 320d may be formed of material which is flexible or pliable, while the rigid sleeve 350d is formed of rigid material, rigidly fixed in the curved configuration shown. By this arrangement, axial movement of the sheath 320 back and forth between its operative position (FIG. 8*a*) and its non-operative position (FIG. 8*b*) may be accomplished while the sheath 320*d* conforms to accommodate the rigid curved configuration of the sleeve 350*d*. Also, in the embodiment shown, the drive shaft 316 is sufficiently flexible to undergo the necessary rotational movement while held in the curved configuration shown.

Although the present invention has been described hereabove with specific reference to a presently preferred configuration and construction of the system 300, it will be appreciated that various modifications deletions additions and alterations may be made to the above-described embodiments without departing from the intended spirit and scope of the invention. For example, the modified distal end 324 of the protective axially moveable outer sheath 320 may be formed in various different configurations which still carry out the intended side-shielding and circulatory flow directing functions described hereabove.

What is claimed is:

1. A device for reducing an ophthalmic lens within the lens capsule of a mammalian eye, said device comprising:
    an elongate probe insertable into the lens capsule, said probe comprising:
    i) an elongate tubular sheath having a lumen;
    ii) a rotatable drive shaft extending longitudinally through said elongate tubular sheath, said drive shaft having a distal end;
    iii) a rotatable lens-reducing head positioned on the distal end of said drive shaft, wherein said rotatable lens-reducing head incorporates an impeller which is configured to draw a flow of fluid toward said lens-reducing head;
    iv) said tubular sheath being configured and positioned, during operation of the device, such that a distal portion of the sheath will shield a portion of the lens-reducing head while allowing the remainder of the head to contact and reduce lens matter.

2. The device of claim 1 further in combination with a drive motor connectable to said drive shaft, to rotatably drive said drive shaft and said lens-reducing head.

3. The device of claim 1 wherein said distal portion of said tubular sheath comprises:
    a first side which extends beyond the distal end of the rotatable lens-reducing head during operation thereby shielding a first side of said lens-reducing head;
    a second side which terminates short of the distal end of the lens-reducing head during operation thereof; and
    a transverse frontal surface which extends from the distal end of the first side of said sheath to the distal end of the second side of said sheath.

4. The device of claim 3 wherein said transverse frontal surface is curved.

5. The device of claim 4 wherein said transverse frontal surface is straight.

6. The device of claim 3 wherein said distal portion of said sheath comprises:
    a tube having a closed distal end which substantially surrounds said lens-reducing head during operation thereof, and which has at least one aperture formed near the closed distal end of said tube to permit said lens-reducing head to contact and reduce lens material through said aperture.

7. The device of claim 1 wherein the distal portion of said tubular sheath is further configured and positioned to shield one side of the lens-reducing head while another side of the lens-reducing head remains unshielded, and such that most of said flow of fluid is exhausted away from said lens-reducing head in the general direction of the side which remains unshielded.

8. The device of claim 1 wherein said device includes means for changing the relative positioning of the lens-reducing head and the tubular sheath between:
    a nonoperative position wherein the lens-reducing head is positioned within the tubular sheath; and,
    an operative position wherein a portion of the lens-reducing head is shielded by a portion of the sheath and the remainder of the lens-reducing head is sufficiently unshielded by the sheath and allowed to contact and reduce lens matter.

9. The device of claim 8 wherein said means for changing the relative positioning of the lens-reducing head and the tubular sheath comprises:
    apparatus for longitudinally moving the tubular sheath back and forth while the rotatable drive shaft and lens-reducing head remain longitudinally stationary.

10. The device of claim 8 wherein said means for changing the relative positioning of the lens-reducing head and the tubular sheath comprises:
    apparatus for longitudinally moving the rotatable drive shaft and lens reducing head back and forth while the tubular sheath remains longitudinally stationary.

11. The device of claim 1 wherein said tubular sheath is rotatable so as to permit the operator to adjust the rotational orientation of the tubular sheath, after the device has been inserted into the lens capsule.

12. The device of claim 1 further comprising:
    a fluid flow passageway extending longitudinally through said probe for infusing fluid into the lens capsule.

13. The device of claim 12 wherein said rotatable drive shaft extends through a non-rotatable tubular sleeve having an outer surface and an inner surface defining a lumen, and wherein said tubular sleeve is disposed longitudinally within the lumen of said tubular sheath, and wherein said fluid flow passageway comprises a space which exists between the inner surface of said tubular sleeve and said rotatable drive shaft.

14. The device of claim 13 further comprising:
    a helical bearing member having a multiplicity of spaced-apart helical convolutions, said bearing member being disposed within the fluid flow passageway provided between the inner surface of said tubular sleeve and the outer surface of said rotatable shaft so as to rotatably hold said shaft in an axially centered position within said sleeve; and,
    whereby, a helical fluid flow passageway is created by the disposition of said helical bearing member within said fluid flow space.

15. The device of claim 14 wherein said helical bearing member is configured such that rotation of said shaft will pump fluid in the distal direction through said helical fluid flow passageway.

16. The device of claim 14 wherein said helical bearing member is divided into a plurality of oppositely wound segments, said oppositely wound segments to deter any pumping effect created by rotation of said drive shaft.

17. The device of claim 13 further comprising a second fluid flow passageway between the outer surface of said sleeve and the inner surface of said tubular sheath.

18. The device of claim 17 wherein at least one fluid/debris inlet aperture is formed in said tubular sheath near the distal end thereof to facilitate suctioning of fluid and debris through said second fluid flow passageway.

19. The device of claim 13 further comprising:
a bulkhead positioned transversely within the tubular sheath, near the distal end thereof;
a central aperture extending longitudinally through said bulkhead;
the lumen of said tubular sleeve being aligned with said aperture such that said rotatable drive shaft which extends through said tubular sleeve also extends through said central aperture, said drive shaft being smaller in diameter than said aperture such that a space exists to allow fluid infused through said fluid flow passageway to flow around said drive shaft, through said central aperture, and out of the distal end of the tubular sheath.

20. The device of claim 19 wherein:
the distal end of the tubular sleeve is in abutment with and supported by said bulkhead to hold the distal end of the sleeve in position within the surrounding tubular sheath with the lumen of said sleeve in axial alignment with said aperture.

21. The device of claim 13 further comprising:
a bulkhead positioned transversely within the lumen of said tubular sheath, near the distal end thereof;
a central aperture extending longitudinally though said bulkhead;
a tubular extension member interposed between the distal end of said drive shaft and said lens-reducing head, said tubular extension member extending longitudinally through the central aperture of said bulkhead and having a lumen, said tubular extension member being rotatable concurrently with rotation of said drive shaft and said lens-reducing head, said tubular extension member having at least one fluid inlet aperture located proximal to said bulkhead and in communication with said first fluid flow space, and at least one fluid outlet aperture located distal to said bulkhead;
said device being thereby operable such that fluid may be infused in the distal direction through the first fluid flow space and through the lumen of said tubular extension member, such that said fluid will flow out of the outlet aperture of said tubular extension member and into a mammalian eye in which said device is inserted.

22. The device of claim 21 wherein said tubular extension member has an outer bearing surface which rides in contact with said central aperture of said bulkhead as said tubular extension member rotates in conjunction with said drive shaft and said lens reducing head.

23. The device of claim 12 further in combination with:
a source of irrigation fluid connected to said fluid flow passageway to facilitate infusion of irrigation fluid through said fluid passageway.

24. The device of claim 1 further comprising:
a fluid flow passageway extending longitudinally through said probe for aspirating fluid and debris from the lens capsule.

25. The device of claim 24 further in combination with:
a source of negative pressure connected to said fluid passageway to aspirate fluid and debris through said fluid passageway.

26. The device of claim 1 wherein said elongate probe is of straight configuration.

27. The device of claim 1 wherein said elongate probe is of curved configuration.

28. The device of claim 1 wherein one of said tubular sheath and said rotatable drive shaft are longitudinally moveable relative to the other to alternately position the rotatable lens-reducing head relative to the tubular sheath in:
a first position wherein the lens-reducing head is positioned within the tubular sheath; and,
a second position wherein at least a portion of the lens-reducing head is sufficiently exposed to contact and reduce lens matter during operation of said device.

29. The device of claim 28 wherein a non-rotating tubular sleeve is mounted about said drive shaft and held in fixed or longitudinal relation to said drive shaft and lens-reducing head, said tubular sleeve extending longitudinally within the lumen of said tubular sheath.

30. The device of claim 29 wherein said elongate probe is of curved configuration and wherein:
said rotatable drive shaft is sufficiently pliable to rotate while in said curved configuration; and,
one of said tubular sheath and said tubular sleeve are formed of rigid material shaped in said curved configuration and the other thereof is formed of material which is sufficiently pliable to conform to said curved configuration as the device is transitioned between said first and second positions.

31. The device of claim 30 wherein said tubular sheath is pliable and said tubular sleeve is rigid.

32. The device of claim 30 wherein said tubular sheath is rigid and tubular sleeve is pliable.

33. A method for reducing an ophthalmic lens within the lens capsule within a mammalian eye, said method comprising the steps of:
a) providing a lens-reducing device which comprises:
i) a tubular sheath having a distal end;
ii) an elongate drive shaft extending longitudinally through said tubular sheath and having a distal end;
iii) a rotating lens-reducing head positioned on the distal end of said drive shaft, the lens-reducing head having an impeller; and
iv) said sheath being configured and positioned, during operation of said device, such that the distal end of the sheath will shield one side of the lens-reducing head, while allowing an unshielded portion of the lens-reducing head to remain sufficiently unshielded to contact and reduce lens matter within the lens capsule;
b) inserting said device into the eye such that the distal end of the sheath is positioned at a non-centered location within the lens capsule;
c) positioning the sheath to cause the shielded side of the lens-reducing head to be located adjacent a selected portion of the lens capsule;
d) rotationally driving the drive shaft and lens-reducing head to effect reduction of the ophthalmic lens, the impeller on the lens-reducing head configured to draw fluid axially toward the distal end.

34. The method of claim 33 wherein step b) further comprises:
inserting the probe at an angle relative to a longitudinal axis of the eye, with the distal end of the probe being located in said non-centered position within the lens capsule.

35. The method of claim 33 wherein step c) further comprises:
positioning said sheath such that the flow of fluid exhausted from the rotating head will be caused to flow around the periphery of the lens capsule.

36. The method of claim 35 wherein the sheath of the device is rotatable, and wherein said positioning of said sheath comprises:

rotating said sheath to cause the distal end of the sheath to become situated such that the unshielded portion of the sheath is directed toward the center of the lens capsule.

37. The method of claim 33 wherein step c) comprises:

rotating said sheath such that the flow of fluid created by rotation of the lens-reducing head will:
i) initially spin the lens in a flat plane within the lens capsule to facilitate initial reduction of a peripheral portion of the lens; and
ii) thereafter cause the remainder of the lens to tumble within the lens capsule to cause repeated contact of the lens with the lens-reducing head, thereby facilitating complete reduction of the remaining portion of the lens.

38. The method of claim 33 further comprising the step of:

infusing a fluid into the lens capsule.

39. The method of claim 33 further comprising the step of:

aspirating fluid and debris from the lens capsule.

40. The method of claim 33 further comprising the step of:

concomitantly infusing fluid into the lens capsule and aspirating fluid and debris from the lens capsule.

41. The method of claim 33 wherein:

the device provided in step a) incorporates means for alternately positioning the lens-reducing head, relative to the sheath, in:
i) a first position whereby the entire lens-reducing head is located within and shielded by the sheath; and
ii) a second position wherein one side of the lens-reducing head is shielded by the distal tip portion of the sheath and a remaining portion of the lens-reducing head is unshielded and capable of contacting and reducing lens matter within the lens capsule; and wherein the method further comprises the steps of:

initially causing the lens-reducing head to be located in said first position during insertion of the probe into the lens capsule; and subsequently causing the lens-reducing head to become positioned in said second position to facilitate reduction of the ophthalmic lens within the lens capsule.

42. The method of claim 41 wherein, prior to insertion of the device in step b, of the method, said method comprises the additional step of:

causing said lens-reducing head to be in said first position relative to said sheath to facilitate insertion of the device into the eye; and, prior to the performance of step d, said method comprises the additional step of:

causing said lens-reducing head to be moved to said second position, relative to said sheath, to facilitate reduction of the ophthalmic lens.

43. The method of claim 42 wherein the step of "causing the lens-reducing head to be placed in said first position relative to the sheath" is accomplished by longitudinally advancing the sheath in the distal direction.

44. The method of claim 42 wherein the step of "causing the lens-reducing head to be located in said second position relative to said sheath" is accomplished by longitudinally retracting said sheath in the proximal direction.

45. A device for reducing an ophthalmic lens within the lens capsule of a mammalian eye, said device comprising:

an elongate probe insertable into the lens capsule, said probe comprising:
i) an elongate tubular sheath having a distal portion comprising:
a first side which extends beyond the distal end of the rotatable lens-reducing head during operation;
a second side which terminates short of the distal end of the lens-reducing head during operation thereof;
a transverse frontal surface which extends from the distal end of the first side of said sheath to the distal end of the second side of said sheath; and
a tube having a closed distal end which substantially surrounds said lens-reducing head during operation thereof, and which has at least one aperture formed near the closed distal end of said tube to permit said lens-reducing head to contact and reduce lens material through said aperture;
ii) a rotatable drive shaft extending longitudinally through said elongate tubular sheath, said drive shaft having a distal end; and
iii) a rotatable lens-reducing head positioned on the distal end of said drive shaft;
iv) said tubular sheath being configured and positioned, during operation of the device, such the first side of the sheath will shield a first side of the lens-reducing head while the second side of the sheath allows a second side of the head to contact and reduce lens matter.

46. A device for reducing an ophthalmic lens within the lens capsule of a mammalian eye, said device comprising:

an elongate probe insertable into the lens capsule, said probe comprising:
i) an elongate tubular sheath;
ii) a rotatable drive shaft extending longitudinally through said elongate tubular sheath, said drive shaft having a distal end;
iii) a rotatable lens-reducing head positioned on the distal end of said drive shaft; and
iv) means for changing the relative positioning of the lens-reducing head and the tubular sheath between:
a nonoperative position wherein the lens-reducing head is positioned within the tubular sheath; and,
an operative position wherein a portion of the lens-reducing head is shielded by a portion of the sheath and the remainder of the lens-reducing head is sufficiently unshielded by the sheath and allowed to contact and reduce lens matter;
v) said tubular sheath being configured and positioned, during operation of the device, such that a distal portion of the sheath will shield a portion of the lens-reducing head while allowing the remainder of the head to contact and reduce lens matter.

47. The device of claim 46 wherein said means for changing the relative positioning of the lens-reducing head and the tubular sheath comprises:

apparatus for longitudinally moving the tubular sheath back and forth while the rotatable drive shaft and lens-reducing head remain longitudinally stationary.

48. The device of claim 46 wherein said means for changing the relative positioning of the lens-reducing head and the tubular sheath comprises:

apparatus for longitudinally moving the rotatable drive shaft and lens reducing head back and forth while the tubular sheath remains longitudinally stationary.

49. A device for reducing an ophthalmic lens within the lens capsule of a mammalian eye, said device comprising:

an elongate probe insertable into the lens capsule, said probe comprising:
  i) an elongate tubular sheath;
  ii) a rotatable drive shaft extending longitudinally through said elongate tubular sheath, said drive shaft having a distal end; and
  iii) a rotatable lens-reducing head positioned on the distal end of said drive shaft;
  iv) said tubular sheath being configured and positioned, during operation of the device, such that a distal portion of the sheath will shield a portion of the lens-reducing head while allowing the remainder of the head to contact and reduce lens matter, and wherein said tubular sheath is rotatable so as to permit the operator to adjust the rotational orientation of the tubular sheath, after the device has been inserted into the lens capsule.

50. A device for reducing an ophthalmic lens within the lens capsule of a mammalian eye, said device comprising:
an elongate probe insertable into the lens capsule, said probe comprising:
  i) an elongate tubular sheath having a lumen;
  ii) a rotatable drive shaft extending longitudinally through said elongate tubular sheath, said drive shaft having a distal end;
  iii) a rotatable lens-reducing head positioned on the distal end of said drive shaft;
  iv) a fluid flow passageway extending longitudinally through said probe for infusing fluid into the lens capsule; and
  v) a non-rotatable tubular sleeve having an outer surface and an inner surface defining a lumen, said tubular sleeve being disposed longitudinally within the lumen of said tubular sheath, said rotatable drive shaft extending through said non-rotatable tubular sleeve, and wherein said fluid flow passageway comprises a space which exists between the inner surface of said tubular sleeve and said rotatable drive shaft;
  vi) said tubular sheath being configured and positioned, during operation of the device, such that a distal portion of the sheath will shield a portion of the lens-reducing head while allowing the remainder of the head to contact and reduce lens matter.

51. The device of claim 50 further comprising a second fluid flow passageway between the outer surface of said sleeve and the inner surface of said tubular sheath.

52. The device of claim 51 wherein at least one fluid/debris inlet aperture is formed in said tubular sheath near the distal end thereof to facilitate suctioning of fluid and debris through said second fluid flow passageway.

53. The device of claim 50 further comprising:
  a bulkhead positioned transversely within the tubular sheath, near the distal end thereof;
  a central aperture extending longitudinally through said bulkhead;
  the lumen of said tubular sleeve being aligned with said aperture such that said rotatable drive shaft which extends through said tubular sleeve also extends through said central aperture, said drive shaft being smaller in diameter than said aperture such that a space exists to allow fluid infused through said fluid flow passageway to flow around said drive shaft, through said central aperture, and out of the distal end of the tubular sheath.

54. The device of claim 53 wherein:
  the distal end of the tubular sleeve is in abutment with and supported by said bulkhead to hold the distal end of the sleeve in position within the surrounding tubular sheath with the lumen of said sleeve in axial alignment with said aperture.

55. The device of claim 50 further comprising:
  a helical bearing member having a multiplicity of spaced-apart helical convolutions, said bearing member being disposed within the fluid flow passageway provided between the inner surface of said tubular sleeve and the outer surface of said rotatable shaft so as to rotatably hold said shaft in an axially centered position within said sleeve; and,
  whereby, a helical fluid flow passageway is created by the disposition of said helical bearing member within said fluid flow space.

56. The device of claim 55 wherein said helical bearing member is configured such that rotation of said shaft will pump fluid in the distal direction through said helical fluid flow passageway.

57. The device of claim 55 wherein said helical bearing member is divided into a plurality of oppositely wound segments, said oppositely wound segments to deter any pumping effect created by rotation of said drive shaft.

58. The device of claim 50 further comprising:
  a bulkhead positioned transversely within the lumen of said tubular sheath, near the distal end thereof;
  a central aperture extending longitudinally through said bulkhead; and
  a tubular extension member interposed between the distal end of said drive shaft and said lens-reducing head, said tubular extension member extending longitudinally through the central aperture of said bulkhead and having a lumen, said tubular extension member being rotatable concurrently with rotation of said drive shaft and said lens-reducing head, said tubular extension member having at least one fluid inlet aperture located proximal to said bulkhead and in communication with said first fluid flow space, and at least one fluid outlet aperture located distal to said bulkhead;
  said device being thereby operable such that fluid may be infused in the distal direction through the first fluid flow space and through the lumen of said tubular extension member, such that said fluid will flow out of the outlet aperture of said tubular extension member and into a mammalian eye in which said device is inserted.

59. The device of claim 55 wherein said tubular extension member has an outer bearing surface which rides in contact with said central aperture of said bulkhead as said tubular extension member rotates in conjunction with said drive shaft and said lens reducing head.

60. A device for reducing an ophthalmic lens within the lens capsule of a mammalian eye, said device comprising:
  an elongate probe of curved configuration insertable into the lens capsule, said probe comprising:
    i) an elongate tubular sheath;
    ii) a rotatable drive shaft extending longitudinally through said elongate tubular sheath, said drive shaft having a distal end; and
    iii) a rotatable lens-reducing head positioned on the distal end of said drive shaft;
    iv) said tubular sheath being configured and positioned, during operation of the device, such that a distal portion of the sheath will shield a portion of the lens-reducing head while allowing the remainder of the head to contact and reduce lens matter.

61. The device of claim 60 wherein said rotatable lens-reducing head incorporates an impeller which is configured to draw a flow of fluid toward said lens-reducing head, and wherein the distal portion of said tubular sheath is further configured and positioned to shield one side of the lens-reducing head while another side of the lens-reducing head remains unshielded, and such that most of said flow of fluid is exhausted away from said lens-reducing head in the general direction of the side which remains unshielded.

62. A device for reducing an ophthalmic lens within the lens capsule of a mammalian eye, said device comprising:

an elongate probe insertable into the lens capsule, said probe comprising:
  i) an elongate tubular sheath having a lumen;
  ii) a rotatable drive shaft extending longitudinally through said elongate tubular sheath, said drive shaft having a distal end; and
  iii) a rotatable lens-reducing head positioned on the distal end of said drive shaft;
  iv) said tubular sheath being configured and positioned, during operation of the device, such that a distal portion of the sheath will shield a portion of the lens-reducing head while allowing the remainder of the head to contact and reduce lens matter;
  v) wherein one of said tubular sheath and said rotatable drive shaft are longitudinally moveable relative to the other to alternately position the rotatable lens-reducing head relative to the tubular sheath in:
    a first position wherein the lens-reducing head is positioned within the tubular sheath; and,
    a second position wherein at least a portion of the lens-reducing head is sufficiently exposed to contact and reduce lens matter during operation of said device.

63. The device of claim 62 wherein a non-rotating tubular sleeve is mounted about said drive shaft and held in fixed or longitudinal relation to said drive shaft and lens-reducing head, said tubular sleeve extending longitudinally within the lumen of said tubular sheath.

64. The device of claim 63 wherein said elongate probe is of curved configuration and wherein:
  said rotatable drive shaft is sufficiently pliable to rotate while in said curved configuration; and,
  one of said tubular sheath and said tubular sleeve are formed of rigid material shaped in said curved configuration and the other thereof is formed of material which is sufficiently pliable to conform to said curved configuration as the device is transitioned between said first and second positions.

65. The device of claim 64 wherein said tubular sheath is pliable and said tubular sleeve is rigid.

66. The device of claim 64 wherein said tubular sheath is rigid and tubular sleeve is pliable.

* * * * *